United States Patent [19]

Gordon et al.

[11] Patent Number: 4,662,695
[45] Date of Patent: May 5, 1987

[54] STATIC GROUNDING BUCKLE

[75] Inventors: Michael E. Gordon, Wayland; Lenard Cohen, Southboro; William Hudspeth, Norwell; Paul Mills, Acton, all of Mass.

[73] Assignee: Plastic Systems, Inc., Marlboro, Mass.

[21] Appl. No.: 832,846

[22] Filed: Feb. 24, 1986

[51] Int. Cl.⁴ .............................................. H01R 4/66
[52] U.S. Cl. .................................... 339/14 R; 24/170; 361/220
[58] Field of Search .............. 339/11, 14 R; 24/68 R, 24/68 T, 71 R, 71 T, 71 J, 170; 361/212, 220, 223, 224

[56] References Cited

U.S. PATENT DOCUMENTS

| | | | |
|---|---|---|---|
| 1,940,491 | 12/1933 | Freitag | 175/265 |
| 2,588,655 | 3/1952 | O'Neill | 24/71 J |
| 3,596,134 | 7/1971 | Burke | 317/2 B |
| 3,857,397 | 12/1974 | Brosseau | 128/384 |
| 4,373,175 | 2/1983 | Mykkanen | 361/220 |
| 4,398,277 | 8/1983 | Christiansen et al. | 361/220 |
| 4,459,633 | 7/1984 | Vandermark | 361/220 |
| 4,475,141 | 10/1984 | Antonevich | 361/220 |
| 4,577,256 | 3/1986 | Breidegam | 361/220 |

OTHER PUBLICATIONS

Semitronics, Descriptive Sheet D5600, date unknown.

Primary Examiner—Eugene F. Desmond

[57] ABSTRACT

A buckle for securing a conductive strap comprises: a conductive base for skin contact and a non-conductive cover pivotally attached to the base, the base having upwardly extending sides and the cover downwardly extending sides encapsulating the sides of the base, conductive attachment means on the cover and a conductive clip member within the cover in electrical conduct with the attachment means and with the base when the cover is closed.

6 Claims, 7 Drawing Figures

U.S. Patent   May 5, 1987   4,662,695
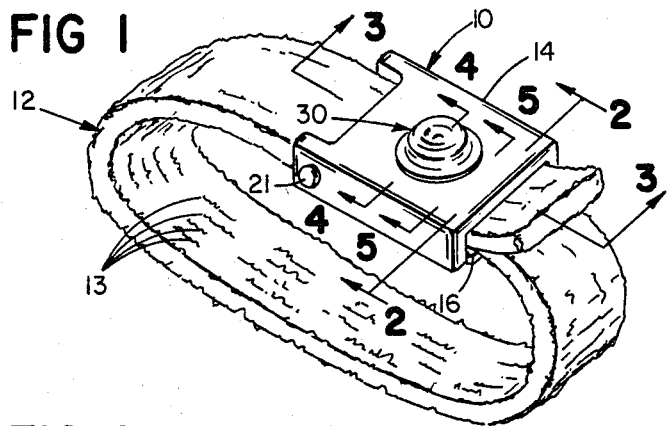
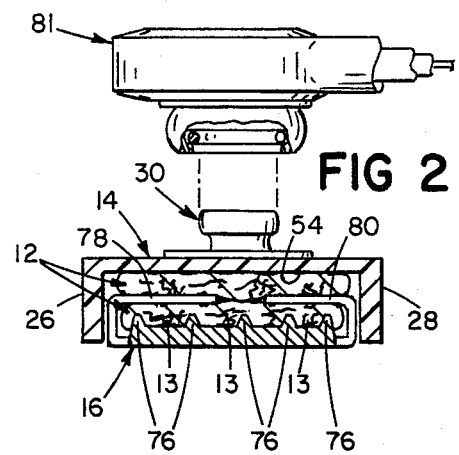
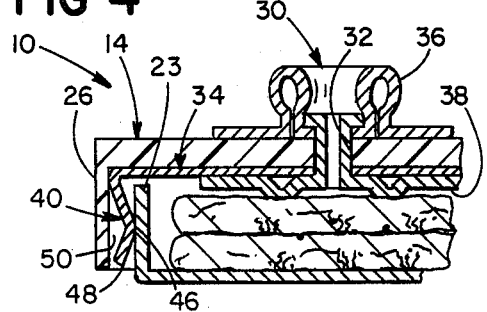
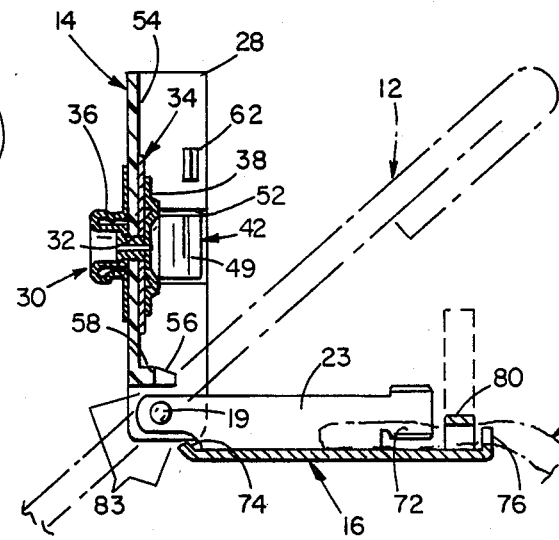
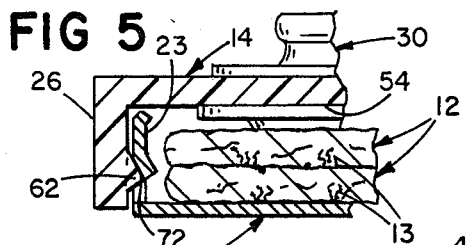
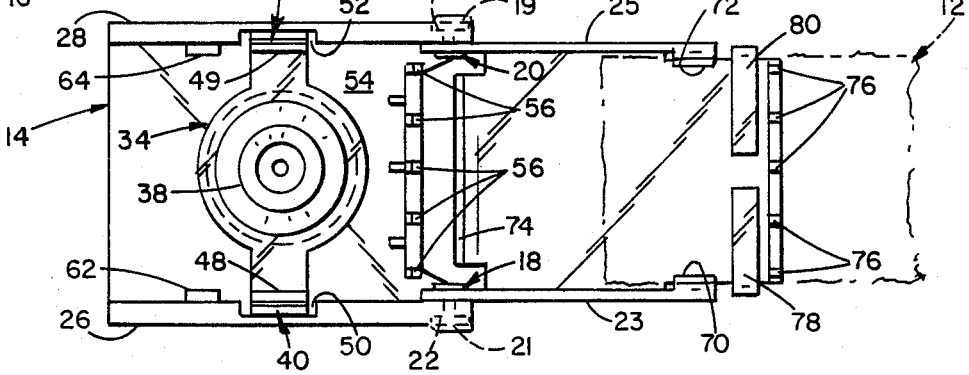
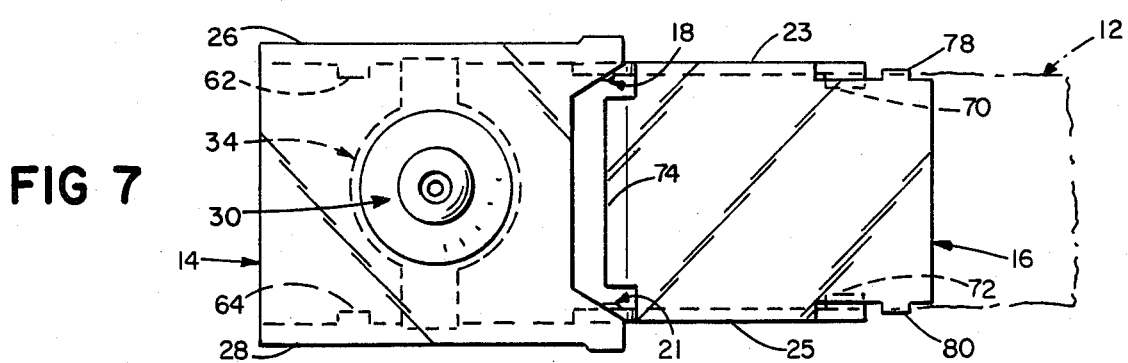

STATIC GROUNDING BUCKLE

BACKGROUND OF THE INVENTION

This invention relates to buckles for static-conductive straps or cuffs.

Some buckles on static-conductive straps are made entirely of metal to provide a complete electrical circuit between the body of the wearer and the grounding means, usually a cord that is attached to the buckle at one end and a grounding point at the other. Some metal buckles open and close to permit adjustment of the diameter of the wrist strap. Other buckles are made of non-conductive material that encloses conductive portions, and a portion of which may be opened to permit adjustment of the length of the strap which adjustment requires trimming of the tail end of the strap.

It is an object of the present invention to provide a buckle for a static-conductive wrist band that will permit both lengthening and shortening of the wrist strap without necessarily requiring trimming and, at the same time, will not cause accidental electrostatic discharge when it comes in contact with, e.g., electronic parts, or electric shock to the wearer in case of inadvertent contact with live electrical circuits.

DESCRIPTION OF THE PREFERRED EMBODIMENT

We first briefly describe the drawings.

DRAWINGS

FIG. 1 is an isometric view of buckle for a static-conductive strap, also shown;

FIG. 2 is a sectional view of the buckle taken along the line 2—2 of FIG. 1 also illustrating a portion of a grounding cord adapted for connection to the buckle;

FIG. 3 is a sectional view of the buckle in an open position taken along the line 3—3 of FIG. 1;

FIG. 4 is a sectional view, partially broken away, of the buckle taken along the line 4—4 of FIG. 1;

FIG. 5 is a sectional view, partly broken away, of the buckle taken along the line 5—5 of FIG. 1.

FIG. 6 is a top view of the buckle, opened;

FIG. 7 is a bottom view of the buckle, opened.

STRUCTURE

Referring to FIG. 1, a buckle 10 for a static conductive strap 12 has an electrically insulating cover 14 made of, e.g., nonconductive nylon, having a surface resistivity in a particular embodiment of from $10^{12}$ to $10^{14}$ ohms per square, and (as more clearly shown in FIGS. 2-7) an electrically conductive metal, e.g., stainless steel, base 16. Strap 12 is a length of woven elasticized nylon that is nonconductive on its outer surface and that has, on its inner surface, interwoven electrically conducting threads 13 made of, e.g., stainless steel fibers or silver-impregnated nylon (e.g., "X-Static" thread manufactured by Sauquoit Industries, Scranton, Pa.). Cover 14 and base 16 are attached to each other in a hinged relationship by hinge rivet pins 18, 20 (FIG. 6), the heads 19, 21 of which are recessed in counter bores 22, 24.

Base 16 has upwardly extending side walls 23, 25; and cover 14 has downwardly extending sides 26, 28 that entirely enclose side walls 23, 25 when buckle 10 is in its closed position (FIG. 1).

Cover 14 has a conductive metal snap stud 30 inserted through cover hole 32 (FIG. 3), and through metal closure clip 34 such that cover 14 and closure clip 34 are closely held between stud top 36 and stud base 38 of snap stud 30, with closure clip 34 in electrically conductive contact with stud base 38.

Closure clip 34 has downwardly projecting tabs 40, 42 each of which has (as shown in FIG. 4) an inward bend and a reverse bend so as to form contact knuckles 46, 47 for resiliently engagingly side walls 23, 25 and closure guides 48, 49. As shown in FIG. 4, each of tabs 40, 42 is recessed into pockets 50, 52 in sides 26, 28.

Referring to FIGS. 3 and 4, the inner surface 54 of cover 14 has a row of downwardly projecting teeth 56 integral with tooth base 58, which is perpendicular to inner surface 54. As shown in FIG. 3, teeth 56 and base 16 cooperate to form gap 83 between them, through which an end of strap 12 is inserted. As shown in FIGS. 3, 5, and 6, cover 14 also has locking lugs 62, 64 on the inner surfaces of sides 26, 28, spaced the same distance from hinge rivet pins 18, 20 as are closure recesses 70, 72 in base 16, such that lugs 62, 64 snap into locking relationship with closure recesses 70, 72 when buckle 10 is closed.

As shown in FIGS. 3, 6, and 7, base 16 has, adjacent hinge pins 18, 20, tail portion 74 that is bent upward from base 16 at an angle of approximately 45°. At the end opposite the hinged end of base 16 is a row of strap anchoring teeth 76 perpendicular to, and integral with base 16. As shown in FIGS. 3 and 4, strap anchoring tabs 78, 80 are integral with base 16, are spaced slightly from anchoring teeth 76, and fold inward transversely over an end of strap 12, thereby holding conductive threads 13 in electrically conductive contact with anchoring teeth 76.

OPERATION

In operation, buckle 10 is opened to pull more or less of strap 12 through gap 83, depending upon the size of the wrist and the snugness of fit desired. Cover 14 is then snapped closed, and the end 81 of a suitable grounding cord, as shown in FIG. 2, having a mating snap for connection to snap stud 30 is attached both to snap stud 30 and, at its other end, to an appropriate grounding means (not shown).

The closing of cover 14 brings contact knuckles 46, 47 into contact side walls 23, 25 thereby providing both a complete electrical path from base 16 to snap stud 30, and friction to keep cover 14 closed in addition to the closure friction provided by the interlock of lugs 62, 64 with closure recesses 70, 72. This electrical path is protected from contact with, e.g., workbench equipment or workpieces by virtue of its being enclosed within nonconductive cover 14. In fact, all conductive portions of buckle 10 when in use are insulated from contact with anything other than the worker's wrist, thereby minimizing the possibility both of a potentially damaging electrostatic discharge event, and of an electrical injury to the worker caused by inadvertent contact with an unprotected electrical circuit.

Static electricity is drained from the worker's body via the electrical circuit provided by conductive threads 13 electrically connected to base 16 by anchoring teeth 76 and/or by the contact of the base itself with the worker's body. Moreover, conductive threads 13 are only on the inner surface of strap 12, insulated from contact with anything other than the worker's wrist and base 16.

When cover 14 is closed, teeth 56 dig into the fabric of strap 12, which is thereby tightly held between teeth 56 and base 16. Tail portion 74 provides additional friction to prevent strap 12 from being pulled from buckle 10. Pulling backward on strap 12 against teeth 56 has the effect of holding cover 14 closed.

We claim:

1. A buckle for a static-conductive strap comprising:
   a conductive base for contact with the body of the wearer, said base having two sides extending upwardly,
   a cover of insulating material pivotally attached to and encapsulating the sides of said base, said cover having downwardly extending sides extending outside the sides of said base,
   electrically conductive attachment means attached to said cover for connection with electrical grounding means, and
   a conductive member attached to and within said cover in electrical contact with said attachment means, said member engaging said base with said cover closed in electrically conductive contact therewith.

2. The buckle of claim 1 further characterized in that said member comprises a clip having downwardly extending engagement means within said cover and the sides thereof for frictionally engaging in electrical contact the sides of said base.

3. The buckle of claim 1 further characterized in that said cover has a transverse row of teeth at its pivoting end that, together with said base, defines a restricted opening for adjustably gripping said static-conductive strap.

4. The buckle of claim 1 further characterized in that said base has a pair of fold-over tabs for holding the inner surface of said strap in electrical contact with said base.

5. The buckle of claim 1 wherein said strap is electrically conductive on its inner surface, and electrically non-conductive on its outer surface.

6. The buckle of claim 1 further characterized in that said conductive member comprises a clip having a knuckle for frictional engagement and electrical contact with, said base.

* * * * *